United States Patent [19]

Sattich

[11] Patent Number: 5,352,838
[45] Date of Patent: Oct. 4, 1994

[54] SELECTIVE PRODUCTION OF ETHYL MERCAPTAN

[75] Inventor: William E. Sattich, Bartlesville, Okla.

[73] Assignee: Phillips Petroleum Company, Bartlesville, Okla.

[21] Appl. No.: 99,642

[22] Filed: Jul. 30, 1993

[51] Int. Cl.$^5$ .................................. C07C 319/04
[52] U.S. Cl. .................................... 568/72
[58] Field of Search ................... 568/72, 67, 61

[56] References Cited

U.S. PATENT DOCUMENTS 3,994,980 11/1976 Kubicek .................. 568/67

OTHER PUBLICATIONS

Reid, Organic Chemistry of Bivalent Sulfur, vol. I, pp. 20–21, 1980.
Reid, Organic Chemistry of Bivalent Sulfur, vol. I, pp. 18–19, 1958.
Allison et al (ACS Div. Petrol. Chem. Ann. Mtg. Atlantic Cit, Sep. 8–13, 1968, vol. 13, pp. 207–209).

*Primary Examiner*—Johann Richter
*Assistant Examiner*—Margaret J. Page
*Attorney, Agent, or Firm*—Lucas K. Shay

[57] ABSTRACT

A process for selectively producing ethyl mercaptan from a reactant mixture such as, for example, refinery fuel gas mixture is provided which comprises contacting, in the presence of a catalyst such as, for example, oxides of cobalt and molybdenum supported on aluminum, the reactant mixture with hydrogen sulfide wherein the reactant mixture contains ethylene and at least one other olefin such as, for example, propylene. The reactant mixture can also contain other components such as, for example, hydrogen, ethane, methane, propylene, or propane, or mixtures thereof.

15 Claims, No Drawings

SELECTIVE PRODUCTION OF ETHYL MERCAPTAN

FIELD OF THE INVENTION

The present invention relates to a process for selective production of ethyl mercaptan by reacting hydrogen sulfide with a gas mixture comprising ethylene and at least one other olefin.

BACKGROUND OF THE INVENTION

It is known that mercaptans can be produced by the reaction of hydrogen sulfide and an olefin in the presence of a catalyst. For example, ethyl mercaptan can be prepared by reaction of pure ethylene and hydrogen sulfide without creating a problem for separation because the desired mercaptan is the only mercaptan product. However, where the reaction mixture comprises more than one olefin such as ethylene and propylene, it is likely to produce both ethyl mercaptan and propyl mercaptans resulting in separation difficulty because these mercaptans cannot be easily separated by a conventional, economics separation means such as, for example, distillation, extraction, filtration, and membrane diffusion. Therefore, it is highly desirable to develop a process for selectively producing ethyl mercaptan from a feed stream comprising, among others, ethylene and propylene.

SUMMARY OF THE INVENTION

An object of the present invention is to provide a process for producing ethyl mercaptan. Another object of the invention is to provide a process for selective production of ethyl mercaptan from a feedstream containing hydrogen, ethylene, and propylene. A further object of the invention is to provide a process for selective production of ethyl mercaptan from a refinery fuel gas comprising hydrogen, methane, ethane, ethylene, propylene, and propane. An advantage of the present invention is that ethyl mercaptan is the only mercaptan produced simplifying the separation of ethyl mercaptan from the reaction mixture. Other objects, advantages and features will become more apparent as the invention is more fully disclosed hereinbelow.

According to the present invention, a process for selective production of ethyl mercaptan from a reactant mixture containing hydrogen, ethylene, and at least one other olefin-containing reactant is provided which comprises contacting, in the presence of a catalyst, the mixture with hydrogen sulfide at a temperature in the range of from about 225° C. to less than about 275° C. under a pressure in the range of from about 50 psig to about 450 psig for a period sufficient to synthesize the ethyl mercaptan.

DETAILED DESCRIPTION OF THE INVENTION

The term "selective production of ethyl mercaptan" is used herein to refer to, unless otherwise indicated, the weight ratio of mercaptans other than ethyl mercaptan to ethyl mercaptan of 0.02 or less.

The process of the present invention can be carried out in a batch mode, a semi-continuous mode or a continuous mode. The choice of a particular process mode is a matter of preference to one skilled in the art and generally depends on available equipment.

The at least one other olefin-containing reactant present in the mixture can be a simple olefin, an aromatic compound having a vinylic structure, or mixtures thereof. Examples of olefin-containing reactants include, but are not limited to, propylene, 1-butene, 2-butene, 1-pentene, 2-pentene, isobutylene, 1,3-butadiene, 1,3-pentadiene, 1,4-pentadiene, styrene, t-butylstyrene, cyclopentene, cyclohexene, 1,3-cyclohexadiene, and mixtures thereof. The mixture can also contain other components such as, for example, methane, ethane, propane, butane, and mixtures thereof. The presently preferred reactant mixture is a refinery fuel gas mixture which contains hydrogen, methane, ethane, ethylene, propane, and propylene. The mole % of any individual gas of this mixture can be in the range from about 0.01% to about 50%. Ethylene contained in the fuel gas mixture is converted to ethyl mercaptan upon contacting with hydrogen sulfide in the presence of a catalyst. Upon separation of the ethyl mercaptan from the reaction mixture, other components of the reaction mixture can again be used as fuel gas.

The presently preferred catalyst is an oxide or sulfide of a metal belonging to Groups IIIB, IVA, VIA, and VIIIA of the Periodic Table of the Elements, including aluminum, titanium, zirconium, molybdenum, and cobalt. The presently preferred catalyst can also be supported on an inorganic material. The presently most preferred catalyst is oxides of cobalt and molybdenum, supported on an inorganic oxide such as alumina.

According to the present invention, the process is carried out at a temperature in the range of from about 225° C. to less than about 275° C., preferably from about 240° C. to about 270° C., and most preferably from 250° C. to 270° C. The pressure of the process can vary widely from about 50 psig to about 450 psig, preferably from about 120 psig to about 400 psig, and most preferably from 150 psig to 350 psig.

In a continuous operation, the feed rate, gas hourly space velocity, of the reactant mixture and hydrogen sulfide is in the range of from about 0.001 to about 1.0, preferably from about 0.1 to about 0.5, and most preferably from 0.2 to 0.3 liter of feed per g of catalyst per hour. The hydrogen sulfide content of the reactant mixture and hydrogen sulfide is in the range of from about 0.01 to about 0.05, preferably from about 0.02 to about 0.04, and most preferably from 0.022 to 0.03 moles/L of gas which includes the reactant mixture and hydrogen sulfide. In a batch process, the amount of catalyst employed ranges from about 0.1 to about 10 weight % of ethylene present in the mixture. Contact time in a batch reactor is generally dependent on the temperature, pressure, reactivity and desired conversion, and is generally in the range of from about 5 minutes to about 10 hours.

Ethyl mercaptan produced in the process of the present invention can be recovered In any conventional manner and can be effected by extracting the product mixture with water.

The following example further illustrates the process of the Invention and is not intended to be construed to limit the scope of the invention.

EXAMPLE

Reactions were conducted by passing a simulated fuel gas mixture and excess hydrogen sulfide ($H_2S$) through a 29 inch long by 11/16 inch inner diameter stainless steel tube (reactor) packed with Engelhard HPC-60K catalyst. Hydrogen sulfide was fed using a precalibrated LAPP-30 pump. The gas mixture was fed using a precalibrated Moore flow controller equipped with a micrometer valve. Pressure was controlled via a back pressure regulator (Moore valve) downstream from the catalyst tube. The catalyst tube was heated with a three-zone electric furnace. The first zone heated a portion of the tube containing only glass beads and was used as a "preheat zone." The latter two zones heated the portion of the tube containing the catalyst. External temperatures were monitored and controlled via three thermocouples (one in the center of each zone) inserted between the inside of the heating furnace and the outside of the catalyst tube and connected to three temperature controllers which controlled the power supply to the heating furnace. Internal catalyst bed temperatures were monitored at the center of each zone via thermocouples inserted through a ¼ inch outer diameter tube in the center of the catalyst tube.

To start a run, the reactor was brought to the desired conditions and allowed to remain at those conditions for at least one hour before any sampling was done. After that time, samples of the effluent gas stream were collected, using a gas-tight syringe, from a septum port just downstream from the back pressure regulator. The gas samples were immediately analyzed by gas chromatography.

The Engelhard HPC-60K catalyst which is commercially available from Engelhard Corporation was in the form of a 1/10 inch cloverleaf extrudate which was characterized as:

| Cobalt | 5.0 | wt % |
|---|---|---|
| Molybdenum | 16.0 | wt % |
| Sodium | 0.04 | wt % |
| Sulfate | 0.1 | wt % |
| Iron | 0.03 | wt % |
| Surface Area | 210 | m$^2$/g |
| Pore Volume | 0.46 | mL/g |
| Density | 0.753 | g/mL |

The results are shown in the following Table.

| Production of Mercaptans From Simulated Fuel Gas Mixture | | | | | | | | | | | |
|---|---|---|---|---|---|---|---|---|---|---|---|
| Run | Temp. °C. | Press psi | Gas Mix$^a$ GHSV$^b$ | H$_2$S WHSV$^c$ | % Conversion | | % Selectivity | | | | Wt Ratio$^h$ |
| | | | | | Ethylene | Propylene | Ethane | EtSH$^d$ | Propane | PrSH$^e$ | |
| 1 | 150 | 150 | 0.14 | 0.24 | 26 | 90 | ND$^g$ | 87 | 10 | 75 | 0.312 |
| 2 | 175 | 150 | 0.14 | 0.24 | 84 | 100 | ND$^g$ | 78 | 20 | 70 | 0.207 |
| 3 | 200 | 150 | 0.23 | 0.24 | 92 | 100 | ND$^g$ | 67 | 45 | 45 | 0.148 |
| 4 | 200 | 150 | 0.23 | 0.48 | 95 | 100 | ND$^g$ | 74 | 20 | 65 | 0.176 |
| 5 | 200 | 150 | 0.23 | 0.48 | 100 | 100 | ND$^g$ | 78 | 20 | 65 | 0.190 |
| 6 | 200 | 350 | 0.14 | 0.24 | 100 | 100 | 6 | 77 | 55 | 40 | 0.098 |
| 7 | 200 | 350 | 0.14 | 0.48 | 100 | 100 | ND$^g$ | 92 | 25 | 75 | 0.120 |
| 8 | 225 | 150 | 0.14 | 0.24 | 98 | 100 | 15 | 58 | 85 | 10 | 0.057 |
| 9 | 250 | 150 | 0.14 | 0.24 | 98 | 100 | 27 | 65 | 100 | 0 | 0.000 |
| 10 | 250 | 150 | 0.14 | 0.48 | 99 | 100 | 10 | 78 | 85 | 10 | 0.020 |
| 11 | 250 | 350 | 0.23 | 0.24 | 100 | 100 | 84 | 14 | 100 | trace$^f$ | 0.005 |
| 12 | 250 | 350 | 0.46 | 0.48 | 99 | 100 | 16 | 59 | 90 | 5 | 0.016 |
| 13 | 300 | 350 | 0.23 | 0.24 | 100 | 100 | 0 | 0 | 100 | 0 | —$^i$ |
| 14 | 75 | 150 | 0.12 | 0.21 | ND$^g$ | 10 | ND$^g$ | trace$^f$ | 10 | 80 | 1.421 |
| 15 | 100 | 150 | 0.12 | 0.21 | ND$^g$ | 50 | ND$^g$ | trace$^f$ | ND$^g$ | 100 | 0.950 |
| 16 | 100 | 150 | 0.12 | 0.21 | ND$^g$ | 25 | ND$^g$ | trace$^f$ | 15 | 80 | 0.693 |
| 17 | 125 | 150 | 0.12 | 0.21 | 14 | 75 | ND$^g$ | 89 | 5 | 75 | 0.489 |
| 18 | 150 | 150 | 0.12 | 0.21 | 28 | 95 | ND$^g$ | 84 | 10 | 75 | 0.315 |
| 19 | 175 | 150 | 0.12 | 0.21 | 71 | 100 | ND$^g$ | 71 | 15 | 70 | 0.219 |
| 20 | 200 | 150 | 0.12 | 0.21 | 100 | 100 | 6 | 61 | 30 | 55 | 0.159 |
| 21 | 200 | 150 | 0.12 | 0.21 | 98 | 100 | ND$^g$ | 58 | 50 | 35 | 0.133 |
| 22 | 200 | 150 | 0.12 | 0.21 | 100 | 100 | 10 | 56 | 40 | 45 | 0.150 |
| 23 | 225 | 150 | 0.12 | 0.21 | 99 | 100 | 20 | 47 | 85 | 10 | 0.048 |
| 24 | 250 | 150 | 0.12 | 0.21 | 100 | 100 | 68 | 28 | 100 | 0 | 0.000 |
| 25 | 250 | 150 | 0.12 | 0.21 | 100 | 100 | 83 | 16 | 100 | 0 | 0.000 |
| 26 | 275 | 150 | 0.12 | 0.21 | 100 | 100 | 100 | 0 | 100 | 0 | —$^i$ |
| 27 | 300 | 150 | 0.12 | 0.21 | 100 | 100 | 100 | 0 | 100 | 0 | —$^i$ |
| 28 | 150 | 0 | 0.04 | 0.41 | 29 | 70 | ND$^g$ | 96 | ND$^g$ | 95 | 0.706 |
| 29 | 150 | 0 | 0.20 | 0.41 | 3 | 30 | ND$^g$ | trace$^f$ | 5 | 90 | 0.641 |
| 30 | 150 | 350 | 0.20 | 0.41 | 42 | 100 | 14 | 79 | 10 | 85 | 0.224 |
| 31 | 200 | 0 | 0.12 | 0.21 | 33 | 45 | 22 | 59 | 35 | 55 | 0.195 |
| 32 | 200 | 150 | 0.12 | 0.21 | 100 | 100 | 18 | 52 | 50 | 35 | 0.133 |
| 33 | 250 | 0 | 0.04 | 0.41 | 85 | 65 | ND$^g$ | 91 | 60 | 25 | 0.139 |
| 34 | 250 | 0 | 0.20 | 0.41 | 59 | 40 | 30 | 52 | 100 | trace$^f$ | 0.084 |
| 35 | 250 | 350 | 0.20 | 0.41 | 100 | 100 | 65 | 29 | 100 | trace$^f$ | 0.001 |

$^a$Gas Mixture Composition (mole %):
40% Hydrogen 6.8 % Nitrogen
27% Methane 1.0% Propylene
13% Ethane 0.2% Propane
12% Ethylene
$^b$Gas Hourly Space Velocity in L/g catalyst/hr.
$^c$Weight Hourly Space Velocity in g/g catalyst/hr.
$^d$Ethyl Mercaptan.
$^e$Isopropyl Mercaptan (trace amounts of n-propyl mercaptan were sometimes detected, but the selectivity could not be accurately detected).
$^f$Trace amounts were detected, but Selectivity could not be accurately determined.
$^g$Not Determined - Conversion or Selectivity was too low to be accurately determined.
$^h$Weight ratio of propyl mercaptans (both isopropyl mercaptan and n-propyl mercaptan) to ethyl mercaptan.
$^i$—, not determined.

Runs 9–12, 24–25, and 35 in the above table illustrate the process of the invention, in which ethyl mercaptan was produced while very little or no isopropyl mercaptan was produced. In these runs, the weight ratio of propyl mercaptans, including isopropyl mercaptan and n-propyl mercaptan were always 0.02 or less, as low as 0. Although other runs (non-invention process) also produced ethyl mercaptan, significant amounts of propyl mercaptans were also produced, even at low propylene conversions (runs 14–16, 29, and 31). Very low weight ratio of mercaptans other than ethyl mercaptan to ethyl mercaptan would greatly facilitate the isolation of ethyl mercaptan from the product mixture. Other gases in the product mixture can be recycled as fuel gas.

The results shown in the above examples clearly demonstrate that the present invention is well adapted to carry out the objects and attain the end and advantages mentioned as well as those inherent therein. While modifications may be made by those skilled in the art, such modifications are encompassed within the spirit of the present invention as defined by the specification and the claims.

That which is claimed is:

1. A process for selective production of ethyl mercaptan from a reactant mixture which comprises hydrogen, ethylene and propylene comprising contacting, in the presence of a catalyst, said mixture with hydrogen sulfide at a temperature in the range of from about 225° C. to about 275° C. under a pressure in the range of from about 50 psig to about 450 psig for a period sufficient to produce said ethyl mercaptan.

2. A process according to claim 1 wherein said reactant mixture further comprises one reactant selected from the group consisting of methane, ethane, propane, and mixtures thereof.

3. A process according to claim 1 further comprising recovering said ethyl mercaptan from the resulting product mixture.

4. A process according to claim 1 wherein said catalyst comprises oxides cobalt and molybdenum wherein said oxides are supported on alumina.

5. A process according to claim 1 wherein said process is carried out at a temperature in the range of from about 240° C. to about 270° C.

6. A process according to claim 5 wherein said temperature is in the range of from 250° C. to 270° C.

7. A process according to claim 1 wherein said process is carried out under a pressure in the range of from about 120 psig to about 400 psig.

8. A process according to claim 7 wherein said pressure is in the range of from 150 psig to 350 psig.

9. A process according to claim 1 wherein said process is carried out by feeding said reactant mixture and said hydrogen sulfide at a rate of from about 0.001 to about 1.0 liter of said reactant mixture and said hydrogen sulfide per gram of said catalyst per hour.

10. A process according to claim 9 wherein said rate is from about 0.1 to about 0.5 liter of said reactant mixture and said hydrogen sulfide per gram of said catalyst per hour.

11. A process according to claim 9 wherein said rate is from 0.2 to 0.3 liter of said reactant mixture and said hydrogen sulfide per gram of said catalyst per hour.

12. A process according to claim 1 wherein said hydrogen sulfide is present in the range of from about 0.01 to about 0.05 moles per liter of gas wherein said gas comprises said reactant mixture and said hydrogen sulfide.

13. A process according to claim 12 wherein said range is from about 0.02 to about 0.04 moles per liter of gas.

14. A process according to claim 13 wherein said range is from 0.022 to 0.03 moles per liter of gas.

15. A process for selective production of ethyl mercaptan from a fuel gas mixture comprising contacting said fuel gas mixture, in the presence of oxides of cobalt and molybdenum, with hydrogen sulfide; wherein said fuel gas mixture comprises hydrogen, methane, ethylene, ethane, propylene, and propane; said oxides are supported on alumina; and said fuel gas mixture has a feed rate in the range of from 0.2 to 0.3 liter of said fuel gas mixture per gram of said catalyst per hour.

* * * * *